(12) United States Patent
Hayes et al.

(10) Patent No.: US 11,090,467 B2
(45) Date of Patent: Aug. 17, 2021

(54) APPARATUS AND METHODS FOR SCAFFOLDING

(71) Applicant: Alucent Biomedical, Inc., Salt Lake City, UT (US)

(72) Inventors: R B Eugene Hayes, Salt Lake City, UT (US); D H Perkins, Salt Lake City, UT (US); Jie Ren, Salt Lake City, UT (US); Robert R. Scott, Salt Lake City, UT (US)

(73) Assignee: Alucent Biomedical, Inc., Salt Lake City, UT (US)

( * ) Notice: Subject to any disclaimer, the term of this patent is extended or adjusted under 35 U.S.C. 154(b) by 91 days.

(21) Appl. No.: 16/150,094

(22) Filed: Oct. 2, 2018

(65) Prior Publication Data

US 2020/0101269 A1     Apr. 2, 2020

(51) Int. Cl.
*A61M 29/00* (2006.01)
*A61M 25/10* (2013.01)
(Continued)

(52) U.S. Cl.
CPC ... *A61M 25/1011* (2013.01); *A61B 17/12136* (2013.01); *A61M 25/104* (2013.01);
(Continued)

(58) Field of Classification Search
CPC .... A61B 17/12136; A61M 2025/1013; A61M 2025/105; A61M 2025/1079;
(Continued)

(56) References Cited

U.S. PATENT DOCUMENTS

| 5,728,068 A | 3/1998 | Leon et al. |
| 6,635,052 B2 | 10/2003 | Loeb |

(Continued)

FOREIGN PATENT DOCUMENTS

| CN | 106691365 | 5/2017 |
| WO | WO 2014/022867 A8 | 2/2014 |

OTHER PUBLICATIONS

David Brieger et al., "Local drug delivery systems and prevention of restenosis", Cardiovascular Research, Feb. 11, 1997, pp. 405-413, Elsevier, United States.

(Continued)

*Primary Examiner* — Rebecca E Eisenberg
(74) *Attorney, Agent, or Firm* — Finnegan, Henderson, Farabow, Garrett & Dunner, LLP (57) ABSTRACT

An apparatus and methods to form a tissue scaffolding are provided. The apparatus may include a catheter shaft extending from a proximal end to a distal tip, a distal balloon positioned on the catheter shaft proximal to the distal tip, and a proximal balloon positioned on the catheter shaft proximal to the distal balloon. The apparatus may further include an intermediate balloon positioned on a distal segment of the catheter shaft proximal to the distal balloon and distal to the proximal balloon. The intermediate balloon and the distal segment each include a translucent material. A light fiber may extend through the distal segment. A first lumen and a second lumen may be arranged in the catheter shaft, the first lumen comprising a first port located between the distal balloon and the intermediate balloon, and the second lumen comprising a second port located between the intermediate balloon and the proximal balloon.

20 Claims, 5 Drawing Sheets

(51) Int. Cl.
*A61B 17/12* (2006.01)
*A61M 5/00* (2006.01)

(52) U.S. Cl.
CPC ....... *A61M 5/007* (2013.01); *A61M 25/10185* (2013.11); *A61M 2025/105* (2013.01); *A61M 2025/1013* (2013.01); *A61M 2025/1079* (2013.01); *A61M 2025/1093* (2013.01); *A61M 2025/1097* (2013.01); *A61M 2205/3337* (2013.01); *A61M 2205/3344* (2013.01)

(58) Field of Classification Search
CPC .. A61M 2025/1093; A61M 2025/1097; A61M 2205/3344; A61M 25/1011
See application file for complete search history.

(56) References Cited

U.S. PATENT DOCUMENTS

| | | | |
|---|---|---|---|
| 6,685,672 | B1 | 2/2004 | Forman |
| 7,396,354 | B2 | 7/2008 | Rynchnovsky et al. |
| 8,088,103 | B2 | 1/2012 | Teeslink et al. |
| 2004/0093044 | A1* | 5/2004 | Rychnovsky .......... A61N 5/062 607/88 |
| 2005/0059930 | A1 | 3/2005 | Garrison et al. |
| 2006/0167439 | A1* | 7/2006 | Kalser .................. A61M 25/10 604/544 |
| 2007/0213761 | A1 | 2/2007 | Murphy et al. |
| 2007/0106216 | A1 | 5/2007 | Noodin |
| 2007/0282301 | A1 | 12/2007 | Segalescu et al. |
| 2010/0280451 | A1* | 11/2010 | Teeslink ................ A61M 5/007 604/99.04 |
| 2012/0259216 | A1 | 10/2012 | Gerrans et al. |
| 2013/0053758 | A1 | 2/2013 | Kibbe |
| 2018/0117292 | A1 | 5/2018 | Sanovas |
| 2018/0344991 | A1 | 12/2018 | Cerchiar et al. |

OTHER PUBLICATIONS

Antonio Fernández-Ortiz et al., "A New Approach for Local Intravascular Drug Delivery. Iontophoretic Balloon", American Heart Association Journals, 1994, pp. 1518-1522, American Heart Association, United States.

JP Kilroy et al., "Localized in vivo model drug delivery with intravascular ultrasound and microbubbles", PubMed, Oct. 2014, Abstract, NCBI, United States.

David E. Newby et al., "Invasive assessment of the coronary circulation: intravascular ultrasound and Doppler", Research Methods in Human Cardiovascular Pharmacology, 2002, pp. 561-575, Blackwell Science Ltd., United Kingdom.

International Search Report and Written Opinion of the International Searching Authority in corresponding International Application No. PCT/US2019/054027 dated Nov. 25, 2019.

International Search Report and Written Opinion of the International Searching Authority in International Application No. PCT/US2020/020262 dated May 18, 2020.

International Search Report and Written Opinion of the International Searching Authority in International Application No. PCT/US2020/044499 dated Oct. 22, 2020.

* cited by examiner

APPARATUS AND METHODS FOR SCAFFOLDING

BACKGROUND

Technical Field

The present disclosure generally relates to apparatus and methods to form a tissue scaffolding. More particularly, and without limitation, the disclosed embodiments relate to catheters, occlusion catheter systems, and methods of occlusion and perfusion using catheter systems to create a natural vessel scaffolding.

Background Description

Balloon catheters are used in a number of surgical applications including occluding blood flow either distally or proximally of a treatment site. The inflation of the balloon must be controlled in order to avoid over expansion or rupture of the balloon, which may rupture or otherwise damage the vessel. Percutaneous Transluminal Angioplasty (PTA), in which a balloon is used to open obstructed arteries, has been widely used to treat atherosclerotic lesions. However, this technique is limited by the vexing problems of re-occlusion and restenosis. Restenosis results from the excessive proliferation of smooth muscle cell (SMC), and the rate of restenosis is above 20%. Thus, about one in five patients treated with PTA must be treated again within several months.

Additionally, stenting is a popular treatment, in which an affected area of the artery having been constricted as a result of progress of arteriosclerosis is mechanically expanded with the aid of a balloon catheter, followed by placement of a metallic stent within the vascular lumen to restore the flow of blood. Constriction or occlusion of the artery is problematic and can be itself, or cause, major health complications. Placement of a metallic stent has been found to result in 20% to 30% of patients requiring postoperative treatment. One cause of this high frequency of required postoperative treatment is vascular intimal hyperplasia within the vascular lumen resulting in lumen narrowing despite the stent being placed. In order to decrease in-stent restenosis, attempts have been made to design a stent of a type having a surface carrying a restenosis-inhibiting drug so that when the stent is placed in an artery, the drug is eluted in a controlled manner within the vascular lumen. Those attempts have led to commercialization of drug-eluting stents (hereinafter referred to as DES) utilizing sirolimus (immunosuppressor) and paclitaxel (cytotoxic antineoplastic drug). However, since those drugs have an effect of inhibiting the proliferation of vascular cells (endothelial cells and smooth muscle cells) by acting on the cell cycle thereof, not only can the vascular intimal hyperplasia resulting from an excessive proliferation of the smooth muscle cells be suppressed, but proliferation is also suppressed of endothelial cells once denuded during placement of the stent, resulting in the adverse effect that the repair or treatment of the intima of a blood vessel becomes reduced. In view of the fact that thrombosis tends to occur more easily at a site less covered with endothelial cells in the intima of a blood vessel, an antithrombotic drug must be administrated for a prolonged time, say, half a year or so and, even though the antithrombotic drug is administrated, the drug will run out and leading to a risk of late thrombosis and restenosis.

The technical problem underlying the present disclosure is therefore to overcome these prior art difficulties by creating devices providing for controlled delivery and aspiration of therapeutic agents to the surrounding tissues, casting the tissue to a final shape, and activating the therapeutic agent in the tissue forming the cast shape and propping the vessel open. The solution to this technical problem is provided by the embodiments characterized in the claims.

SUMMARY

The embodiments of the present disclosure include catheters, catheter systems, and methods of forming a tissue scaffolding using catheter systems. Advantageously, the exemplary embodiments allow for controlled delivery and aspiration of therapeutic agents to the surrounding tissues, casting the tissue to a final shape, and activating the therapeutic agent in the tissue forming the cast shape and propping the vessel open.

According to an embodiment of this disclosure, an apparatus is provided. The apparatus may include a catheter shaft extending from a proximal end to a distal tip, a distal balloon positioned on the catheter shaft proximal to the distal tip, and a proximal balloon positioned on the catheter shaft proximal to the distal balloon. The proximal balloon may be in fluid communication with the distal balloon. The apparatus may further include an intermediate balloon positioned on a distal segment of the catheter shaft proximal to the distal balloon and distal to the proximal balloon. The intermediate balloon and the distal segment each include a translucent material. A light fiber may be positioned in the catheter shaft and extend through the distal segment. A first lumen and a second lumen may be arranged in the catheter shaft, the first lumen comprising a first port located between the distal balloon and the intermediate balloon, and the second lumen comprising a second port located between the intermediate balloon and the proximal balloon. A pressure sensor may be positioned in one of the first or second lumen and not coincident with either the first or second port.

In some embodiments, the translucent material of the intermediate balloon is transparent. The translucent material of the distal segment may be transparent, and the catheter shaft may include a translucent material that is transparent.

In some embodiments, the proximal balloon and the distal balloon may be expandable to occlude an area of a vessel between the proximal balloon and the distal balloon. The light fiber provides light activation through the distal segment and the intermediate balloon. The fluid communication between the proximal balloon and the distal balloon selectively expands the proximal balloon and the distal balloon in concert. The intermediate balloon is expanded separately from and after the proximal balloon and the distal balloon.

In some embodiments, the first port is in fluid communication with a drug source, the drug source supplying a drug through the first port and into a blood vessel of a subject. The intermediate balloon is expanded after the drug is supplied through the first port, and the expansion of the intermediate balloon facilitates uniform drug delivery in the blood vessel of the subject. The intermediate balloon is expanded after the drug is supplied through the first port, and the light fiber is activated and provides light transmission through the distal segment and the intermediate balloon to activate the drug in the blood vessel. The second port removes an excess of a drug from a blood vessel of a subject. In some embodiments, the apparatus includes one or more fluid communication ports positioned between the proximal balloon and the distal balloon.

In some embodiments, the light fiber is positioned in a guidewire lumen of the catheter shaft. In other embodiments, the light fiber is positioned in an inflation lumen of the catheter shaft.

According to another embodiment of this disclosure, a method of tissue scaffolding in a blood vessel of a subject is provided. The method includes providing a catheter into the blood vessel. The catheter may include a catheter shaft extending from a proximal end to a distal tip; a distal balloon positioned on the catheter shaft proximal to the distal tip; a proximal balloon positioned on the catheter shaft proximal to the distal balloon, the proximal balloon in fluid communication with the distal balloon; an intermediate balloon positioned on a distal segment of the catheter shaft proximal to the distal balloon and distal to the proximal balloon, the intermediate balloon and the distal segment each comprising a translucent material; a light fiber positioned in the catheter shaft and extending through the distal segment; an first lumen and a second lumen coaxially arranged in the catheter shaft, the first lumen comprising an first port located between the distal balloon and the intermediate balloon, and the second lumen comprising a second port located between the intermediate balloon and the proximal balloon; and a pressure sensor positioned in one of the first or second lumen not coincident with either the first or second. The method may further include expanding the distal balloon and the proximal balloon into contact with the blood vessel thereby occluding the blood vessel; supplying a drug from a drug source through at least one of the first and second ports into a blood vessel of a subject; expanding the intermediate balloon into contact with the blood vessel; activating the light fiber thereby providing light transmission through the distal segment and the intermediate balloon to activate the drug in the blood vessel.

In some embodiments, the translucent material of the intermediate balloon is transparent. The translucent material of the distal segment may be transparent, and the catheter shaft may include a translucent material that is transparent.

In some embodiments, the proximal balloon and the distal balloon are expandable to occlude an area of a vessel between the proximal balloon and the distal balloon. The expanding of the intermediate balloon supports a wall of the blood vessel. The fluid communication between the proximal balloon and the distal balloon selectively expands the proximal balloon and the distal balloon in concert. The intermediate balloon is expanded separately from and after the proximal balloon and the distal balloon.

According to another embodiment of this disclosure, an apparatus is provided. The apparatus includes a catheter shaft positioned in a blood vessel of a subject, the catheter shaft extending from a proximal end to a distal tip; a distal balloon positioned on the catheter shaft proximal to the distal tip; a proximal balloon positioned on the catheter shaft proximal to the distal balloon, the proximal balloon in fluid communication with the distal balloon, the distal balloon and the proximal balloon are configured to expand into contact with the blood vessel thereby occluding the blood vessel; an intermediate balloon positioned on a distal segment of the catheter shaft proximal to the distal balloon and distal to the proximal balloon, the intermediate balloon and the distal segment each comprising a transparent material, the intermediate balloon configured to expand into contact with the blood vessel; a light fiber positioned in the catheter shaft and extending through the distal segment, the light fiber configured to provide light transmission through the distal segment and the intermediate balloon; a first lumen and a second lumen coaxially arranged in the catheter shaft, the first lumen comprising a first port located between the distal balloon and the intermediate balloon, and the second lumen comprising a second port located between the intermediate balloon and the proximal balloon; and a pressure sensor positioned in the infusion lumen not coincident with both the infusion port and the aspiration port; and a drug source configured to supply a drug through the infusion port into the blood vessel.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Reference will now be made in detail to embodiments and aspects of the present disclosure, examples of which are illustrated in the accompanying drawings. Where possible, the same reference numbers will be used throughout the drawings to refer to the same or like parts.

Figure 1:
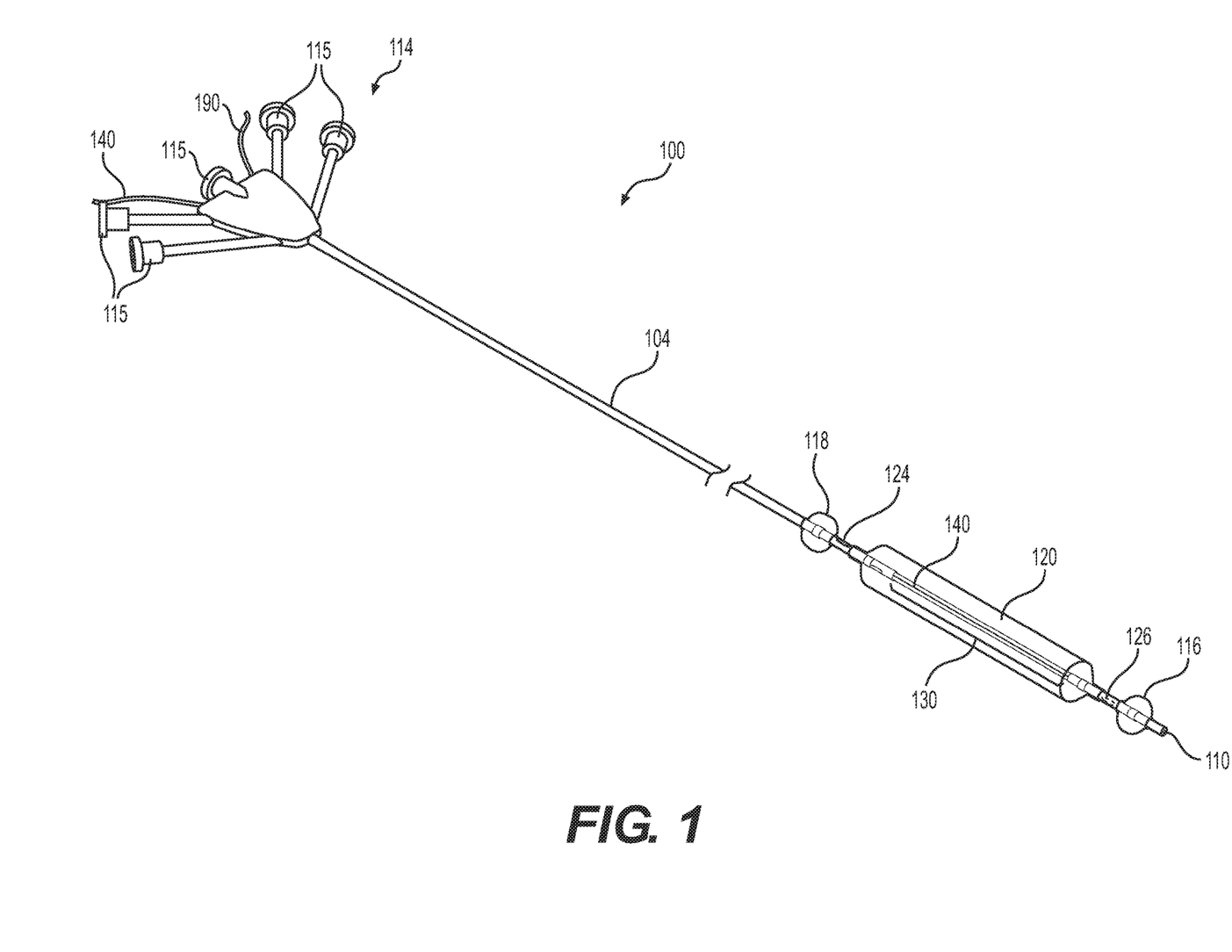
FIG. 1 is a perspective view of an exemplary catheter, according embodiments of the present disclosure.
Figure 2:
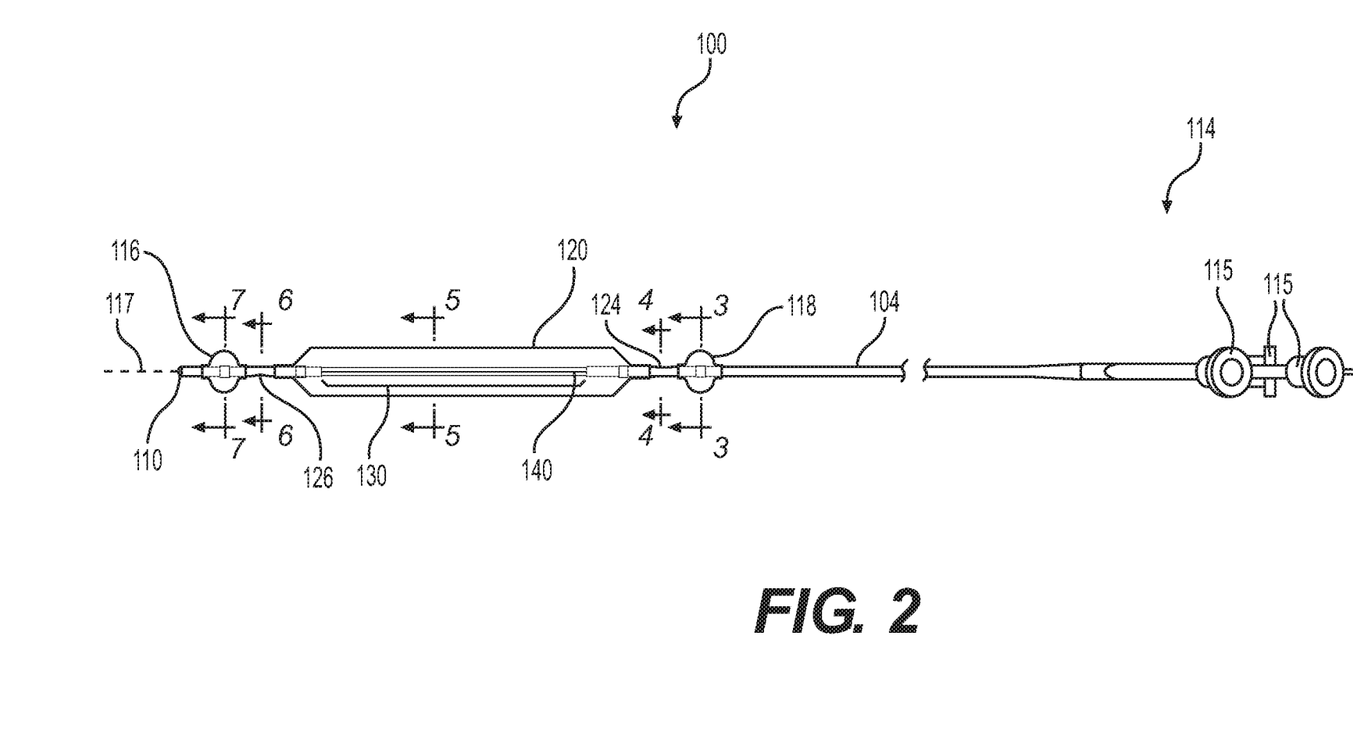
FIG. 2 is a side elevational view of the exemplary catheter of FIG. 1.

FIGS. 1 and 2 illustrate an exemplary catheter assembly 100 in accordance with an embodiment of this disclosure. The catheter assembly 100 having a catheter shaft 104 that extends from a proximal end 106 to a distal tip 110 of the catheter assembly 100. The catheter assembly 100 may be configured for longitudinal movement and positioning within a vessel (e.g. blood vessel) of a subject. In some embodiments, the catheter assembly 100 may be configured for occlusion of the vessel and treatment of an area of the vessel. For example, the catheter assembly may be configured for occlusion of a blood vessel and delivery of a drug to the occluded area of the vessel and forming and casting a shape in the vessel, as will be described in more detail below.

The catheter shaft 104 may be made of materials including, but not limited to polymers, natural or synthetic rubber, metal and plastic or combinations thereof, nylon, Pebax, nylon/Pebax blend, Hytrel® and polyethylene. The shaft materials can be selected so as to maximize column strength to the longitudinal length of the shaft. Further, the shaft materials can be braided, so as to provide sufficient column strength. The shaft materials can also be selected so as to allow the device to move smoothly along a guide wire. The catheter shaft 104 can also be provided with a lubricious coating as well as antimicrobial and antithrombogenic coatings. The shaft materials should be selected so as not to interfere with the efficacy of the agent to be delivered or collected. This interference may take the form of absorbing the agent, adhering to the agent or altering the agent in any way. The catheter shaft 104 of the present disclosure may be between about 2-16 French units ("Fr." where one French equals ⅓ of a millimeter, or about 0.013 inches). The catheter shafts to be used in coronary arteries may be between about 3-5 Fr. in diameter, and more specifically may be 3 Fr. The catheter shafts to be used in peripheral vessels may be between about 5-8 Fr. in diameter, and more specifically 5 Fr. The catheter shafts to be used in the aorta may be between about 8-16 Fr. in diameter, and more specifically 12 Fr.

The catheter assembly 100 may include a proximal end connector 114 positioned at the proximal end of the catheter assembly, and the catheter shaft 104 may extend in a distal direction therefrom. The catheter shaft 104 may define a plurality of lumens that are accessible via a plurality of ports 115 of the proximal end connector 114. The plurality of ports 115 may extend angularly away from a longitudinal axis 117 of the catheter shaft 104 and may be configured to engage with external sources desirable to communicate with the plurality of lumens. The ports may engage with external sources via a variety of connection mechanisms, including, but not limited to, syringes, over-molding, quick-disconnect connectors, latched connections, barbed connections, keyed connections, threaded connections, or any other suitable mechanism for connecting one of the plurality of ports 115 to an external source. Non-limiting examples of external sources may include inflation sources (e.g. saline solutions), gaseous sources, treatment sources (e.g. medication, drugs, or any desirable treatment agents discussed further below), light sources, among others. In some embodiments, catheter assembly 100 can be used with a guide wire (not shown), via guide wire lumen 150 (see FIGS. 3-7), to assist in guiding the catheter shaft 104 to the target area of the vessel.

A distal balloon 116 may be positioned on the catheter shaft 104 enveloping a radiopaque marker and proximal to the distal tip 110 along the longitudinal axis 117 of the catheter shaft 104. In some embodiments, the distal balloon 116 may be proximally offset from the distal tip 110 at a distance along the longitudinal axis 117 between 0 mm and 1 mm, 0 mm and 2 mm, 0 mm and 3 mm, 0 mm and 10 mm, or 0 and 50 mm. A proximal balloon 118 may be positioned on the catheter shaft 104 enveloping a radiopaque marker and proximal to the distal balloon 116, and the proximal balloon 118 may be in fluid communication with the distal balloon 116 via an inflation lumen 160. One or more fluid communication ports may be positioned between the proximal balloon 118 and the distal balloon 116 to selectively control fluid communication between the proximal balloon 118 and the distal balloon 116. In some embodiments, a proximal fluid communication port may be smaller (i.e. have a smaller diameter) than a distal fluid communication port. The inflation lumen 160 may extend through the catheter shaft 104 and have an input at one of the plurality of ports 115 of the proximal end connector 114. Fluid communication between the proximal balloon 118 and the distal balloon 116 may selectively expand and contract the proximal balloon 118 and the distal balloon 116 in concert.

In some embodiments, the distal balloon 116 and the proximal balloon 118 may inflate to 2 to 10 millimeters (mm) in diameter. In other embodiments, the distal balloon 116 and the proximal balloon 118 may inflate to 3 to 5 centimeters (cm) in diameter. The distal balloon 116 and the proximal balloon 118 may have a length of about 1 to 2 centimeters (cm) and may take any shape suitable for occluding and sealing a blood vessel of the subject when a compliant or semi-compliant balloon is inflated. Non-limiting examples of shapes the inflated balloons may form include oblong, football-shaped, spherical, ellipsoidal, or may be selectively deformable in symmetric or asymmetric shapes. The force exerted against a vessel interior by each the distal balloon 116 and the proximal balloon 118 may be strong enough to hold the catheter assembly 100 in a stationary position within the vessel or other hollow body structure and provide an adequate seal to control blood or fluid flow. However, the force is not so great as to damage the interior surface of the vessel or other hollow body structure.

The proximal balloon 118 and the distal balloon 116 may be manufactured from materials including, but not limited to Kraton®, nylon, polyurethane, polyolefin or any other biocompatible, elastomeric material, or other soft materials. The materials of the balloons may be selected to maximize pliability and reduce the risk of tissue damage. The balloon materials are selected to not interfere with the efficacy of a therapeutic agent to be delivered or collected. In some embodiments, inflation sources for the proximal balloon 118 and the distal balloon 116 may be syringes or inflation devices connected to at least one of the plurality of ports 115 placing the inflation source in communication with the inflation lumen 160 or other inflation sources. The syringes or inflation devices—individually or separately—may contain contrast media or gas or other fluids effective for inflating the balloon.

Intermediate balloon 120 may be positioned over a distal segment 130 of the catheter shaft 104 proximal to the distal balloon 116 and distal to the proximal balloon 118. In some embodiments, the intermediate balloon 120 may be proximally offset from the distal balloon 116 at a distance along the longitudinal axis 117 between 0 mm and 1 mm, 0 mm and 2 mm, 0 mm and 3 mm, 0 mm and 10 mm, or 0 and 50 mm. The intermediate balloon 120 may further be distally offset from the proximal balloon 118 at a distance along the longitudinal axis 117 between 0 mm and 1 mm, 0 mm and 2 mm, 0 mm and 3 mm, 0 mm and 10 mm, or 0 and 50 mm. The intermediate balloon 120 may be in fluid communication with an inflation source via an intermediate balloon inflation lumen 164 separate from the inflation lumen 160 associated with the proximal balloon 118 and distal balloon 116. The intermediate balloon inflation lumen 164 may extend through the catheter shaft 104 and have an input at one of the plurality of ports 115 of the proximal end connector 114. Fluid communication between the intermediate balloon 120 and the inflation source via the intermediate balloon inflation lumen 164 may cause the intermediate balloon 120 to selectively inflate and deflate separately from and independently of the proximal balloon 118 and the distal balloon 116.

In some embodiments, the intermediate balloon 120 may inflate to 2 to 10 millimeters (mm) in diameter. In other embodiments, the intermediate balloon 120 may inflate to 2 to 4 cm in diameter. The intermediate balloon 120 may have a length of about 0.5 to 1 centimeters (cm), 1 to 2 cm, 1 to 3 cm, or 1 to 5 cm, and may take any shape suitable for supporting a wall of a blood vessel of the subject when the non compliant or semi-compliant balloon is inflated. For example, the intermediate balloon 120 may expand into a cylindrical shape surrounding the distal segment 130 of the catheter shaft 104. The cylindrical shape may be gradually tapered inward at a proximal end and a distal end of the intermediate balloon 120, thereby providing a gradually tapered proximal end and distal end of the intermediate balloon 120 that taper into contact with and become flush with the catheter shaft 104. Non-limiting examples of shapes the inflated intermediate balloon 120 may form include a cylindrical shape, football-shaped, spherical, ellipsoidal, or may be selectively deformable in symmetric or asymmetric shapes so as to limit the potential difference in the treated vessel shape and the untreated vessel shape reducing edge effects common between two surfaces of different stiffness as found in metal stents. The force exerted against a vessel interior by intermediate balloon 120 may be strong enough to scaffold the vessel wall with the catheter assembly 100 held in a stationary position within the vessel or other hollow body structure. However, the force is not so great as to damage the interior surface of the vessel or other hollow body structure.

The intermediate balloon 120 may be manufactured from transparent materials including, but not limited to Kraton®, polyurethane, nylon, polyethylene terephthalate (PET), polyolefin or any other biocompatible, elastomeric material, or other soft materials. The materials of the intermediate balloon 120 may be selected to maximize pliability and reduce the risk of tissue damage, and to allow light transmission through the material. The intermediate balloon 120 materials are selected to not interfere with the efficacy of the agent to be delivered or collected. In some embodiments, inflation sources for the intermediate balloon 120 may be a syringe connected to at least one of the plurality of ports 115 placing the inflation source in communication with the inflation lumen 160, or other inflation sources. The syringes—individually or separately—may contain contrast media or gas or other fluids effective for inflating the balloon. Similarly, the distal segment 130 may be manufactured from transparent materials that allow light transmission though the distal segment 130.

The catheter assembly 100 may further include a light fiber 140 positioned in the catheter shaft and extending through the distal segment 130 that may be transparent and identified with a proximal and distal radiopaque bands 192. The light fiber 140 may transmit light through the distal segment 130 and the intermediate balloon 120. In some embodiments, the light fiber 140 may be a plurality of light fibers 140 surrounding the guidewire lumen 150. The light fiber 140 may be connected to the proximal end connector 114 and may have proximal ends that connect to a light fiber activation source via at least one of the plurality of ports 115. In some embodiments, the light fibers 140 may be configured to transmit light at a wavelength of 375 nanometers (nm) to 475 nm, and more specifically 450 nm that transmits through the distal segment 130 and the intermediate balloon 120. In some embodiments, the light fiber 140 may be positioned in the guidewire lumen 150 as shown in FIGS. 11-14. In other embodiments, the light fiber 140 may be positioned in the inflation lumen 160. In other embodiments, the light fiber 140 may be positioned in the intermediate balloon inflation lumen 164 as shown in FIGS. 3-7.

A proximal port 124 may be positioned distal to the proximal balloon 118 and proximal to the intermediate balloon 120. The proximal port 124 may be an opening that extends from an interior lumen (e.g. infusion lumen 154) through the catheter shaft 104 thereby selectively placing the interior lumen in fluid communication with the exterior of the catheter shaft 104 between the proximal balloon 118 and the intermediate balloon 120. A distal port 126 may be positioned proximal to the distal balloon 116 and distal to the intermediate balloon 120. The distal port 126 may be an opening that extends from an interior lumen (e.g. aspiration lumen 158), different from the interior lumen connected to the proximal port, through the catheter shaft 104 thereby selectively placing the interior lumen in fluid communication with the exterior of the catheter shaft 104 between the distal balloon 116 and the intermediate balloon 120.

The proximal port 124 and the distal port 126 can each take any number of shapes, including, but not limited to, oblong, circular, rectangular, square, triangular, or any other shape suitable for providing fluid communication into and out of the catheter shaft 104. The proximal port 124 and the distal port 126 may be positioned on opposing sides of the catheter shaft 104. For example, the proximal port 124 may be positioned on a representative top side of the catheter shaft 104 (as illustrated in FIG. 1) and the distal port 126 may be positioned on a representative bottom side of the catheter shaft 104 (not shown in FIG. 1). In some embodiments, the proximal port 124 and the distal port 126 may be positioned on the same side of the catheter shaft 104 such that the proximal port 124 and the distal port 126 are aligned on the catheter shaft 104. In still other embodiments, the proximal port 124 and the distal port 126 may be positioned at any angular position around the circumference of the catheter shaft 104. For example, the proximal port 124 may be positioned on the representative top surface of the catheter shaft 104 and the distal port 126 may be located on a representative side surface of the catheter shaft 104 where the distal port 126 is at a position rotated 90 degrees from the proximal port 124. In still other embodiments, the proximal port 124 and the distal port 126 may be placed at customized radial positions with respect to each other where the proximal port 124 and the distal port 126 can each be placed at any radial position around the circumference of the catheter shaft 104. The positions of the proximal port 124 and the distal port 126 discussed here may be interchangeable. That is, in one example, the proximal port 124 may be positioned on the representative bottom surface and the distal port 126 may be positioned on the representative top surface. Of course, the interchangeability of radial positions of the proximal port 124 and the distal port 126 applies to each example.

In some embodiments, the proximal port 124 may be an infusion port configured to deliver a treatment through the catheter shaft 104 to the treatment area of the subject. In other embodiments, the distal port 126 may be the infusion port. The infusion port may be in fluid communication with a drug source, the drug source may supply a drug through the infusion port and into a blood vessel of a subject.

In some embodiments, the distal port 126 may be an aspiration port configured to draw fluid from the treatment area through the aspiration port and into the aspiration lumen 158. In other embodiments, the proximal port 124 may be the aspiration port. In other embodiments, the distal port 126 and the proximal port 124 share the same lumen, the infusion lumen 154 or the aspiration lumen 158, the distal port 126 may be in fluid communication with proximal port 124. The aspiration port may be in fluid communication with an external drain where the fluid drawn from the treatment area can be removed from the catheter assembly 100.

FIGS. 3-7 and FIGS. 11-15 show various cross-sectional views through the catheter assembly 100 illustrating a plurality of lumens extending through the catheter shaft 104. The catheter shaft 104 may be the outermost lumen and may provide support to the other lumens. A guide wire lumen 150 may be centrally positioned through the catheter shaft 104 and may be configured to receive a guide wire (not shown) therethrough. The guide wire lumen 150 may also receive light fiber 140 therein, as shown in FIGS. 11-14. Alternatively, or additionally, the light fiber 140 may be received in an inflation lumen, for example intermediate balloon inflation lumen 164, as shown in FIGS. 3-6. The light fiber 140 may also be received in the inflation lumen 160, the aspiration lumen 158, or the infusion lumen 154. Additionally, more than one light fiber 140 may be employed. For example, multiple light fibers 140 may be received in the catheter assembly 100 and may be received in any of the lumens 150, 154, 158, 160, and 164. Alternatively, or additionally, the light liber 140 may be integrated within the wall of the guide wire lumen 150, the infusion lumen 154, or the aspiration lumen 158. The guide wire lumen 150 may extend from the proximal end 106 through the distal tip 110 of the catheter assembly 110.

An infusion lumen 154 may be coaxially arranged in the catheter shaft 104 and extend from a proximal end 106 of the catheter assembly to the infusion port. The infusion lumen 154 may be positioned outside of the guidewire lumen 150 which may be positioned at a more internal position of the catheter shaft 104 than the infusion lumen 154. The infusion lumen 154 may be in fluid communication with an infusion source that may provide a therapeutic agent through the infusion lumen and out of the infusion port into the treatment area of the subject.

Therapeutic agents useful with the device of the present disclosure include any one of or a combination of several agents which are gas, liquid, suspensions, emulsions, or solids, which may be delivered or collected from the vessel for therapeutic or diagnostic purposes. Therapeutic agents may include biologically active substances, or substances capable of eliciting a biological response, including, but not limited to endogenous substances (growth factors or cytokines, including, but not limited to basic fibroblast growth factor, acidic fibroblast growth factor, vascular endothelial growth factor, angiogenic factors), viral vectors, DNA capable of expressing proteins, sustained release polymers, and unmodified or modified cells. Therapeutic agents may include angiogenic agents which induce the formation of new blood vessels. Therapeutic agents may also include anti-stenosis or anti-restenosis agents which are used to treat the narrowing of blood vessel walls. Therapeutic agents may include light-activated agents such as light-activated anti-stenosis or light-activated anti-restenosis agents that may be used to treat the narrowing of blood vessel walls.

An aspiration lumen 158 may be coaxially arranged in the catheter shaft 104 and extend from a proximal end 106 of the catheter assembly to the aspiration port. The aspiration lumen 158 may be positioned outside of the guidewire lumen 150 which may be positioned at a more internal position of the catheter shaft 104 than the aspiration lumen 158. The aspiration lumen 158 may be in fluid communication with the treatment area of the subject and an external drain where the fluid drawn from the treatment area can be removed from the catheter assembly 100 through the aspiration port and through the aspiration lumen 158 and out of the catheter assembly 100 to the external drain.

An inflation lumen 160 may be coaxially arranged in the catheter shaft 104 and extend from a proximal end 106 of the catheter assembly 100 to the proximal balloon 118 and the distal balloon 116. The inflation lumen 160 may be positioned outside of the guidewire lumen 150 which may be positioned at a more internal position of the catheter shaft 104 than the inflation lumen 160. The inflation lumen 160 may be in fluid communication with the proximal balloon 118 and the distal balloon 116 and may provide fluid communication between the proximal balloon 118 and the distal balloon 116 to selectively inflate and deflate the proximal balloon 118 and distal balloon 116. The proximal balloon 118 and distal balloon 116 may selectively expand in concert due to the inflation lumen 160 placing the proximal balloon 118 and the distal balloon 116 in fluid communication with each other.

An intermediate balloon inflation lumen 164 may be coaxially arranged in the catheter shaft 104 and extend from a proximal end 106 of the catheter assembly 100 to the intermediate balloon 120. The intermediate balloon inflation lumen 164 may be positioned outside of the guidewire lumen 150 which may be positioned at a more internal position of the catheter shaft 104 than the intermediate balloon inflation lumen 164. The intermediate balloon inflation lumen 164 may be in fluid communication with the intermediate balloon 120 to selectively inflate and deflate the intermediate balloon 120.

Figure 3:
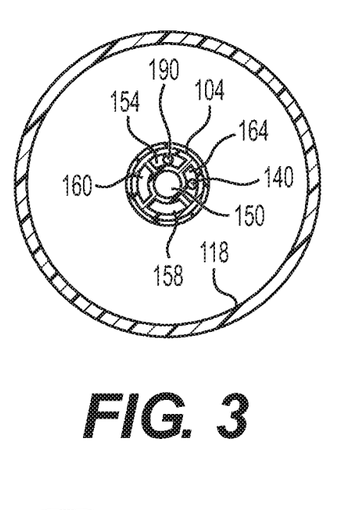
FIG. 3 is a cross-sectional view taken along line 3-3 of FIG. 2.
Figure 4:
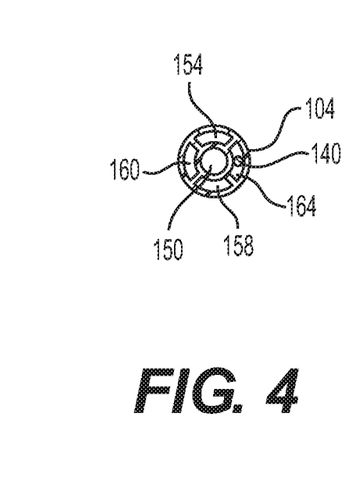
FIG. 4 is a cross-sectional view taken along line 4-4 of FIG. 2.
Figures 5, 6:
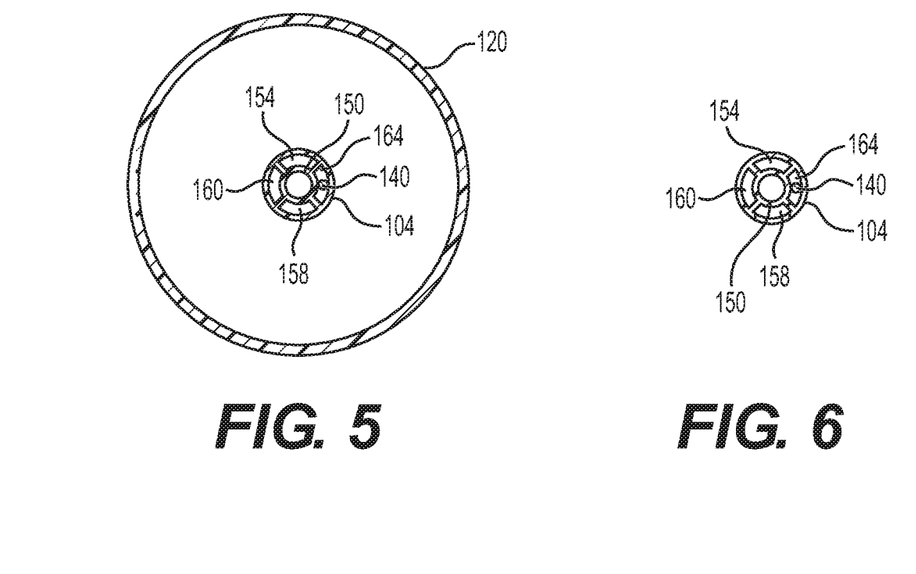
FIG. 5 is a cross-sectional view taken along line 5-5 of FIG. 2.
FIG. 6 is a cross-sectional view taken along line 6-6 of FIG. 2.
Figure 7:
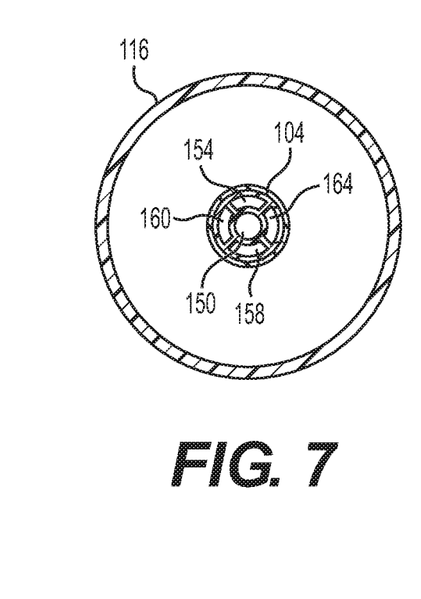
FIG. 7 is a cross-sectional view taken along line 7-7 of FIG. 2.

A pressure sensor 190 may be positioned infusion lumen 154 between the proximal balloon 118 and the distal balloon 116 and extend to a position proximal to the infusion port and may not be coincident with both the proximal port 124 and the distal port 126, as shown in FIG. 3. That is, the pressure sensor 190 may be positioned sufficiently away from the proximal port 124 and the distal port 126. The pressure sensor 190 may alternatively positioned in the aspiration lumen 158 and extend to a position proximal to the aspiration port. The pressure sensor may be positioned away from the proximal port 124 and the distal port 126 so that the pressure sensor may sense the pressure in treatment area or vessel without being affected by fluid flowing into or out of the proximal port 124 and the distal port 126, as pressure readings coincident with the proximal port 124 and the distal port 126 may not be reflective of the pressure within the treatment area or vessel. Accordingly, the pressure of the fluid environment at any point within the treatment area or vessel may be known or estimated. The pressure sensor 190 may provide a user of the catheter assembly 100 with a pressure reading or an estimate of the pressure experienced by a therapeutic agent within the treatment area or vessel. The pressure reading may be relevant for driving the therapeutic agent to the site of action uniformly within the vessel in a time-controlled fashion and to limit vessel damage.

Figure 11:
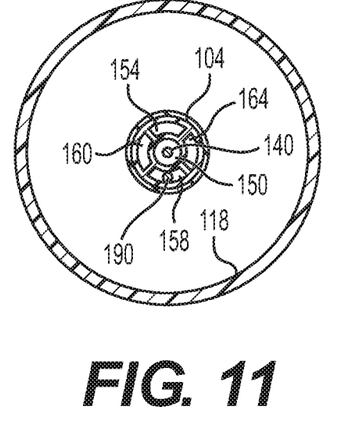
FIG. 11 is another embodiment of a cross-sectional view taken along line 3-3 of FIG. 2.
Figure 12:
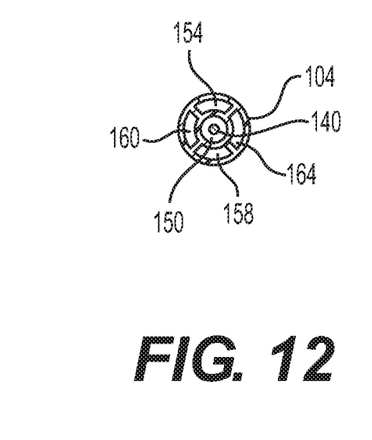
FIG. 12 is another embodiment of a cross-sectional view taken along line 4-4 of FIG. 2.
Figure 13:
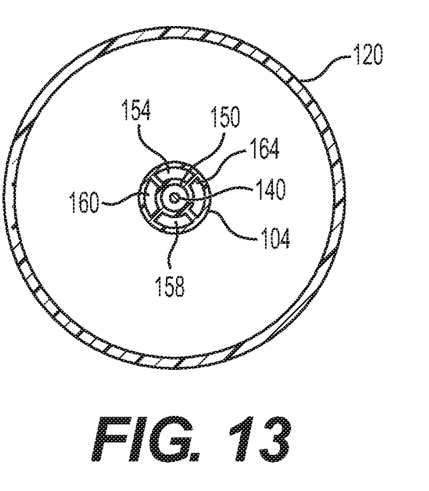
FIG. 13 is another embodiment of a cross-sectional view taken along line 5-5 of FIG. 2.
Figure 14:
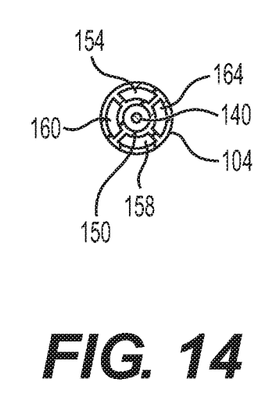
FIG. 14 is another embodiment of a cross-sectional view taken along line 6-6 of FIG. 2.
Figure 15:
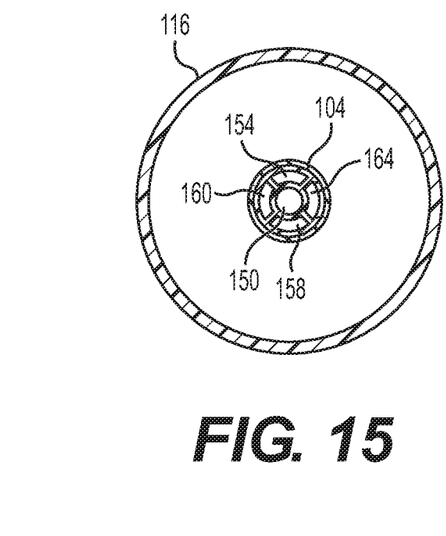
FIG. 15 is another embodiment of a cross-sectional view taken along line 7-7 of FIG. 2.

A second pressure sensor may be positioned between the proximal balloon 118 and the intermediate balloon 116. In some embodiments, the second pressure sensor may be placed in the aspiration lumen 158 when the pressure sensor 190 is placed in the infusion lumen 154. In some embodiments, the second pressure may be placed in the infusion lumen 154 when the pressure sensor 190 is placed in the aspiration lumen 158, as shown in FIG. 11. In some embodiments, when the infusion lumen 154 and the aspiration lumen 158 are in fluid communication, the first and second pressure sensor may be placed in infusion lumen 154 or aspiration lumen 158 together, one between the proximal balloon 118 and the intermediate balloon 120 and one between the intermediate balloon 120 and the distal balloon 116. In some embodiments, the second pressure sensor may be positioned in the aspiration lumen 158 between the proximal balloon 118 and the distal balloon 116 and may not be coincident with both the proximal port 124 and the distal port 126. That is, the pressure sensor may be positioned sufficiently away from the proximal port 124 and the distal port 126. The pressure sensor may be positioned away from the proximal port 124 and the distal port 126 so that the pressure sensor may sense the pressure in treatment area or vessel without being affected by fluid flowing into or out of the proximal port 124 and the distal port 126, as pressure readings coincident with the proximal port 124 and the distal port 126 may not be reflective of the pressure within the treatment area or vessel. Accordingly, the pressure of the fluid environment at any point within the treatment area or vessel may be known or estimated. The pressure sensor may provide a user of the catheter assembly 100 with a pressure reading comparison to the first pressure sensor or an estimate of the pressure experienced by a therapeutic agent within the treatment area or vessel. The pressure reading may be relevant for knowing the pressure differential inside the treatment area and the pressure driving the therapeutic agent to the site of action uniformly within the vessel in a time-controlled fashion and to limit vessel damage.

Figure 8:
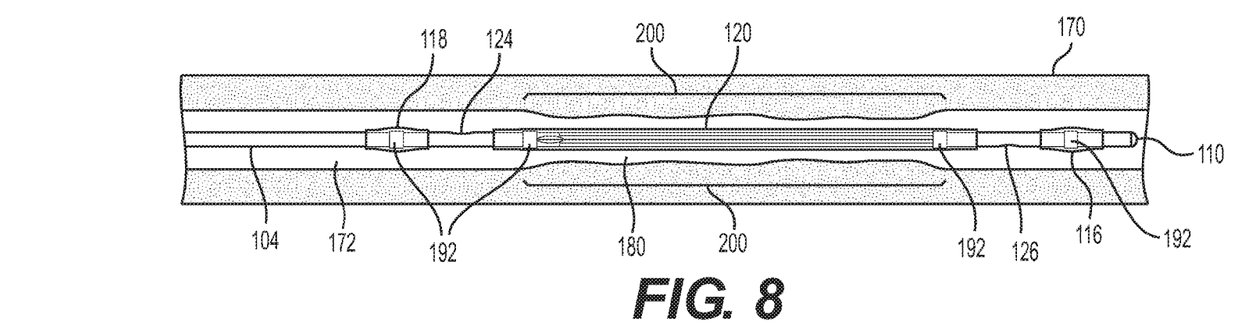
FIG. 8 is side elevation view of an exemplary catheter positioned in a representative blood vessel of a subject.
Figure 9:
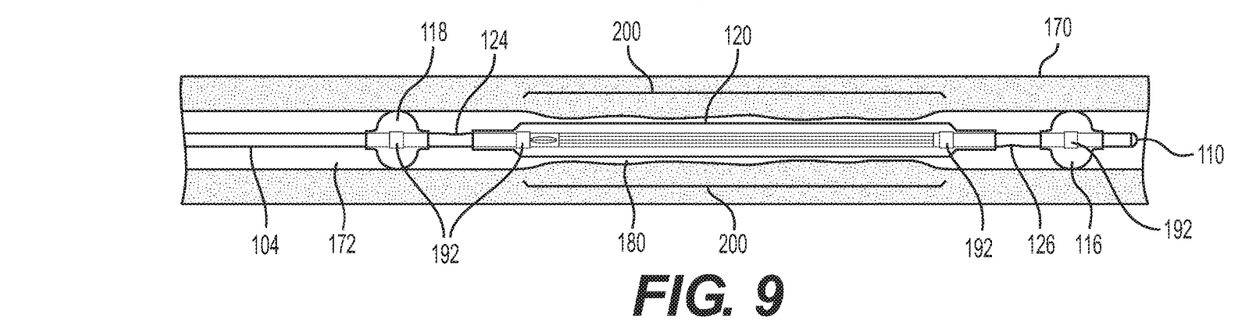
FIG. 9 is a side elevation view of the exemplary catheter of FIG. 8 with an intermediate balloon in a partially-expanded state.

Now that the components of the catheter assembly 100 have been described, the respective functions of the components can be understood. FIGS. 8 and 9 show the distal balloon 116 and the proximal balloon 118 inflated inside a vessel 170 or other hollow body structure. The distal balloon 116, the proximal balloon 118, the intermediate balloon 120, the catheter shaft 104, and other components of the catheter assembly 100 may be dimensioned appropriately to account for the dimensions that would be required in other hollow body structures (non-limiting examples include the aorta, vessels of the lymphatic system, the gastroesophageal tract, the portal-caval system of the liver, the gall bladder and bile ducts, the urinary system, the respiratory system, ducts of the endocrine and exocrine organs, and reproductive organs).

As seen in FIG. 8, the distal balloon 116 and proximal balloon 118 may be inflated within a lumen 172 of a blood vessel 170, without inflation of the intermediate balloon 120. The inflated distal balloon 116 and inflated proximal balloon 118 contact a vessel endothelium and occlude an intraluminal space 180. With the intraluminal space occluded, a small amount (e.g. less than half the total dosage) of the treatment agent may be infused through the infusion port into the treatment area. The intermediate balloon 120 may be aligned with and partially inflated into near-contact with a diseased or blockage area 200 in the vessel 170, and not into contact with the vessel 170, as shown in FIG. 9. With the intermediate balloon 120 partially inflated and not in contact with the vessel wall, a remainder of the therapeutic agent may be delivered. With the vessel 170 occluded by the proximal balloon 118 and the distal balloon 116, the therapeutic agent may be delivered to the treatment area through the infusion lumen 154 and the infusion port. The rate of therapeutic agent delivery to the treatment area may be selected to minimize tissue damage. The rate of therapeutic agent delivery may depend on the size of the infusion port and the pressure under which the agent is passed through the infusion lumen 154 through the infusion port. The rate of therapeutic agent delivery can be controlled by, for example, an osmotic pump or an infusion pump attached in line with the infusion lumen 154 connection at the proximal end connector 114. The use of a perfusion pump may also be also compatible with a two- or three-way valve or check valve appropriately in line with such an arrangement. The therapeutic agent may be present in the treatment area and may perfuse chemically and physically into the treatment area for any desired amount of time or pressure before the intermediate catheter 120 is expanded.

Figure 10:
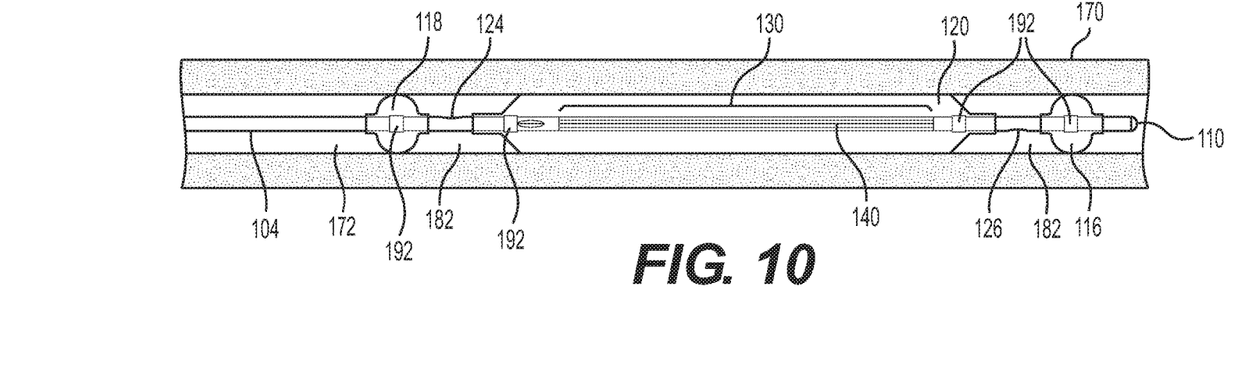
FIG. 10 is a side elevation view of the exemplary catheter of FIG. 8 with an intermediate balloon in an expanded state.

Subsequent additional inflation of the intermediate balloon 120, as shown in FIG. 10, reduces the intraluminal volume exterior to the proximal balloon 118, distal balloon 116, and intermediate balloon 120 to produce occlusion of a comparatively small intraluminal space 182, and thus reduces the treatment volume of the targeted vessel segment. The term "treatment volume" refers to the volume of the vessel, between the inflated proximal balloon 118 and distal balloon 116, minus the volume of the intermediate balloon 120. Consequently, deflation of the intermediate balloon 120 leads to increased treatment volume while inflation of the intermediate balloon 120 reduces the treatment volume. The force exerted against a vessel interior by each the distal balloon 116 and the proximal balloon 118 may be strong enough to hold the catheter assembly 100 in a stationary position within the vessel or other hollow body structure and provide an adequate seal to control blood or fluid flow.

The intermediate balloon 120 may be expanded (FIG. 10) after the treatment agent is supplied through the infusion port. The intermediate balloon 120 may be expanded into contact with the vessel endothelium, which may consequently contact the diseased or blockage area 200, such as a collection of sclerotic plaque within the vessel. The expansion of the intermediate balloon 120 may facilitate uniform delivery of the therapeutic agent in the blood vessel of the subject by forcing the agent outwardly and reducing the treatment area volume, distributing the same therapeutic agent volume over a smaller space. With the therapeutic agent delivered and the intermediate balloon 120 expanded and opposed to the vessel wall, the desired shape is set and prepared for activation, the light fiber 140 may be activated. The light fiber 140 may provide light transmission through the distal segment 130 and the intermediate balloon 120 (due to their transparency) to activate the therapeutic agent in the blood vessel. The activated therapeutic agent may form a chemical lattice that forms an in-situ stent or natural vessel scaffolding. The aspiration port may remove an excess of the therapeutic agent from the treatment area in the blood vessel of a subject before the light activation. For example, the excess therapeutic agent may be drawn out of the treatment area through the aspiration port, into the aspiration lumen 158 and out of the catheter assembly 100.

Another embodiment of this disclosure includes an exemplary method of forming and casting a natural vessel scaffolding in a blood vessel of a subject. The method may include providing a catheter into the blood vessel, the catheter may include similar features to or may be the catheter assembly 100 discussed above. Accordingly, the catheter (e.g. catheter assembly 100) may include a catheter shaft (e.g. catheter shaft 104) extending from a proximal end (e.g. proximal end 106) to a distal tip (e.g. distal tip 110). A distal balloon (e.g. distal balloon 116) may be positioned on the catheter shaft proximal to the distal tip, and a proximal balloon (e.g. proximal balloon 118) may be positioned on the catheter shaft proximal to the distal balloon. The proximal balloon may be in fluid communication with the distal balloon. An intermediate balloon (e.g. intermediate balloon 120) may be positioned on a distal segment (e.g. distal segment 130) of the catheter shaft proximal to the distal balloon and distal to the proximal balloon, the intermediate balloon and the distal segment may each include a transparent material. A light fiber (e.g. light fiber 140) may be positioned in the catheter shaft and extend through the distal segment. An infusion lumen (e.g. infusion lumen 154) and an aspiration lumen (e.g. aspiration lumen 158) may be coaxially arranged in the catheter shaft, the infusion lumen may include an infusion port and the aspiration lumen may include an aspiration port. A pressure sensor (e.g. pressure sensor described above) may be positioned in the infusion lumen not coincident with the infusion port and/or the aspiration port. The method may further include expanding the distal balloon and the proximal balloon into contact with the blood vessel thereby occluding the blood vessel. The method may include supplying a drug from a drug source through the infusion port into a blood vessel of a subject. The method may include expanding the intermediate balloon into contact with the blood vessel. For example, the intermediate balloon 120 may be expanded into contact with the vessel endothelium, which may consequently may contact a diseased or blockage area, such as a collection of sclerotic plaque within the vessel. The expansion of the intermediate balloon 120 may facilitate uniform delivery of the therapeutic agent in the blood vessel of the subject. The method may include activating the light fiber thereby providing light transmission through the distal segment and the intermediate balloon to activate the drug in the blood vessel. For example, with the intermediate balloon 120 expanded and the therapeutic agent delivered, the light fiber 140 may be activated. The light fiber 140 may provide light transmission through the distal segment 130 and the intermediate balloon 120 (due to their transparency) to activate the therapeutic agent in the blood vessel.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An apparatus comprising
   a catheter shaft extending from a proximal end to a distal tip;
   a distal balloon positioned on the catheter shaft proximal to the distal tip;
   a proximal balloon positioned on the catheter shaft proximal to the distal balloon, the proximal balloon in fluid communication with the distal balloon;
   an intermediate balloon positioned on a distal segment of the catheter shaft proximal to the distal balloon and distal to the proximal balloon, the intermediate balloon and the distal segment each comprising a translucent material, the intermediate balloon configured to expand into contact with a blood vessel;
   a light fiber positioned in the catheter shaft and extending through the distal segment;
   a first lumen and a second lumen arranged in the catheter shaft, the first lumen comprising a first port located between the distal balloon and the intermediate balloon, and the second lumen comprising a second port located between the intermediate balloon and the proximal balloon; and
   a pressure sensor positioned in one of the first or second lumen and not coincident with either the first or second port.

2. The apparatus of claim 1 wherein:
   the translucent material of the intermediate balloon is transparent.

3. The apparatus of claim 1 wherein:
   the translucent material of the distal segment is transparent; and
   the catheter shaft comprising a translucent material that is transparent.

4. The apparatus of claim 1 further comprising:
   the proximal balloon and the distal balloon are expandable to occlude an area of a vessel between the proximal balloon and the distal balloon.

5. The apparatus of claim 1 wherein:
   the light fiber provides light activation through the distal segment and the intermediate balloon.

6. The apparatus of claim 1 wherein:
the fluid communication between the proximal balloon and the distal balloon selectively expands the proximal balloon and the distal balloon in concert.

7. The apparatus of claim 1 wherein:
the intermediate balloon is expanded separately from and after the proximal balloon and the distal balloon.

8. The apparatus of claim 1 wherein:
the first port is in fluid communication with a drug source;
the drug source is configured to supply a drug through the first port, the first port in fluid communication with a blood vessel of a subject.

9. The apparatus of claim 8 wherein:
the intermediate balloon is configured to expand after the drug is supplied through the first port;
wherein expansion of the intermediate balloon facilitates uniform drug delivery in the blood vessel of the subject.

10. The apparatus of claim 8 wherein:
the intermediate balloon is configured to expand after the drug is supplied through the first port; and
the light fiber is configured to be activated and provide light transmission through the distal segment and the intermediate balloon to activate the drug in the blood vessel.

11. The apparatus of claim 1 wherein:
the second port removes an excess of a drug from a blood vessel of a subject.

12. The apparatus of claim 1 further comprising:
one or more fluid communication ports positioned between the proximal balloon and the distal balloon.

13. The apparatus of claim 1 wherein:
the light fiber is positioned in a guidewire lumen of the catheter shaft.

14. The apparatus of claim 1 wherein:
the light fiber is positioned in an inflation lumen of the catheter shaft.

15. A method of tissue scaffolding in a blood vessel of a subject, the method comprising:
providing a catheter into the blood vessel, the catheter comprising:
a catheter shaft extending from a proximal end to a distal tip;
a distal balloon positioned on the catheter shaft proximal to the distal tip;
a proximal balloon positioned on the catheter shaft proximal to the distal balloon, the proximal balloon in fluid communication with the distal balloon;
an intermediate balloon positioned on a distal segment of the catheter shaft proximal to the distal balloon and distal to the proximal balloon, the intermediate balloon and the distal segment each comprising a translucent material;
a light fiber positioned in the catheter shaft and extending through the distal segment;
a first lumen and a second lumen coaxially arranged in the catheter shaft, the first lumen comprising an first port located between the distal balloon and the intermediate balloon, and the second lumen comprising a second port located between the intermediate balloon and the proximal balloon; and
a pressure sensor positioned in one of the first or second lumen not coincident with either the first or second;
expanding the distal balloon and the proximal balloon into contact with the blood vessel thereby occluding the blood vessel;
supplying a drug from a drug source through at least one of the first and second ports into a blood vessel of a subject;
expanding the intermediate balloon into contact with the blood vessel, the expanding of the intermediate balloon supports a wall of the blood vessel;
activating the light fiber thereby providing light transmission through the distal segment and the intermediate balloon to activate the drug in the blood vessel.

16. The method of claim 15 wherein:
the translucent material of the intermediate balloon is transparent.

17. The catheter of claim 15 wherein:
the translucent material of the distal segment is transparent.

18. The catheter of claim 15 wherein:
the fluid communication between the proximal balloon and the distal balloon selectively expands the proximal balloon and the distal balloon in concert.

19. The catheter of claim 15 wherein:
the intermediate balloon is expanded separately from and after the proximal balloon and the distal balloon.

20. An apparatus comprising
a catheter shaft positioned in a blood vessel of a subject, the catheter shaft extending from a proximal end to a distal tip;
a distal balloon positioned on the catheter shaft proximal to the distal tip;
a proximal balloon positioned on the catheter shaft proximal to the distal balloon, the proximal balloon in fluid communication with the distal balloon, the distal balloon and the proximal balloon are configured to expand into contact with the blood vessel thereby occluding the blood vessel;
an intermediate balloon positioned on a distal segment of the catheter shaft proximal to the distal balloon and distal to the proximal balloon, the intermediate balloon and the distal segment each comprising a transparent material, the intermediate balloon configured to expand into contact with the blood vessel;
a light fiber positioned in the catheter shaft and extending through the distal segment, the light fiber configured to provide light transmission through the distal segment and the intermediate balloon;
a first lumen and a second lumen coaxially arranged in the catheter shaft, the first lumen comprising a first port located between the distal balloon and the intermediate balloon, and the second lumen comprising a second port located between the intermediate balloon and the proximal balloon;
a pressure sensor positioned in the infusion lumen not coincident with both the infusion port and the aspiration port; and
a drug source configured to supply a drug through the infusion port into the blood vessel.

* * * * *